(12) United States Patent
Jacquot et al.

(10) Patent No.: US 8,951,946 B2
(45) Date of Patent: Feb. 10, 2015

(54) DICARBOXYLIC ACID DIESTERS, NOTABLY THOSE PREPARED FROM FUSEL OILS

(75) Inventors: Roland Jacquot, Francheville (FR); Philippe Marion, Vernaison (FR); Jean-Emile Zanetto, Paris (FR); Olivier Jentzer, Vourles (FR); Sophie Deroo, L'Hay les Roses (FR); Dominique Labarre, Neuilly sur Seine (FR)

(73) Assignee: Rhodia Operations, Abuervilliers (FR)

( * ) Notice: Subject to any disclaimer, the term of this patent is extended or adjusted under 35 U.S.C. 154(b) by 269 days.

(21) Appl. No.: 12/738,971

(22) PCT Filed: Oct. 21, 2008

(86) PCT No.: PCT/EP2008/064179
§ 371 (c)(1),
(2), (4) Date: Jun. 21, 2010

(87) PCT Pub. No.: WO2009/053347
PCT Pub. Date: Apr. 30, 2009

(65) Prior Publication Data
US 2010/0292121 A1    Nov. 18, 2010

(30) Foreign Application Priority Data

Oct. 22, 2007 (FR) ..................... 07 07367

(51) Int. Cl.
| | | |
|---|---|---|
| *C11D 1/66* | (2006.01) | |
| *C11D 3/20* | (2006.01) | |
| *C11D 3/44* | (2006.01) | |
| *C07C 69/42* | (2006.01) | |
| *C07C 69/34* | (2006.01) | |
| *C07C 69/40* | (2006.01) | |
| *C07C 69/44* | (2006.01) | |
| *C09D 9/00* | (2006.01) | |
| *C09K 3/32* | (2006.01) | |
| *C11D 7/26* | (2006.01) | |
| *C23G 5/032* | (2006.01) | |
| *C11D 7/50* | (2006.01) | |

(52) U.S. Cl.
CPC ............... *C07C 69/42* (2013.01); *C07C 69/34* (2013.01); *C07C 69/40* (2013.01); *C07C 69/44* (2013.01); *C09D 9/005* (2013.01); *C09K 3/32* (2013.01); *C11D 7/266* (2013.01); *C23G 5/032* (2013.01); *C11D 7/5022* (2013.01)

USPC ........... 510/119; 510/130; 510/136; 510/137; 510/138; 510/477; 510/488; 510/505

(58) Field of Classification Search
USPC ......... 510/119, 130, 136, 137, 138, 505, 477, 510/488
See application file for complete search history.

(56) References Cited

U.S. PATENT DOCUMENTS

| 4,110,626 A | 8/1978 | Katada et al. |
|---|---|---|
| 4,904,814 A | 2/1990 | Frei et al. |
| 2002/0183575 A1 | 12/2002 | Morini et al. |
| 2007/0286828 A1 | 12/2007 | Deswartvaegher et al. |

FOREIGN PATENT DOCUMENTS

| EP | 0743358 A1 | 11/1996 |
|---|---|---|
| FR | 2878157 A1 | 5/2006 |
| GB | 1041334 A | 9/1996 |

OTHER PUBLICATIONS

English language Machine Language translation of EP 743358.*
Guoqiang et al., "Synthesis of Saturated Fatty Glutarate Using Heteropoly Acid as Catalyst", Journal of Fushun Petroleum Institute, Jun. 1999, pp. 24-28, vol. 19, No. 2.
Cohen et al., "Aliphatic Esters, Properties and Lubricant Applications", Industrial and Engineering Chemistry, pp. 1766-1775, 1953, vol. 45.
Rigg et al., "Autoxidation of Saturated Aliphatic Diesters", Journal of the American Chemical Society, 1953, pp. 1415-1420, vol. 75.
James et al., "Arenesulfonic Acids as Catalysts in the Alcoholysis of Nitriles to Esters", Notes, Journal of Organic Chemistry, 1958, pp. 1225-1227, vol. 23.
Konig et al., "Gas chromatographic separation of chiral 2-hydroxy acids and 2-alkyl-substituted carboxylic acids", Journal of Chromatography, 1980, pp. 292-296, vol. 195.
Laeckmann et al., "Synthesis and Biological Evaluation of Aroylguanidines Related to Amiloride as Inhibitors of the Human Platelet Na$^+$/H$^+$ Exchanger", Bioorganic & Medicinal Chemistry, 2002, pp. 1793-1804, vol. 10.
Xue et al., "Transformation of Amides into Esters by the Use of Chlorotrimethylsilane" Journal of the Chinese Chemical Society, Jan. 2004, pp. 359-362, vol. 51, No. 2.

* cited by examiner

*Primary Examiner* — Gregory R Delcotto
(74) *Attorney, Agent, or Firm* — Dentons US LLP

(57) ABSTRACT

Novel dicarboxylic acid diesters and admixture thereof have the formula (I):

$$R^1\text{—OOC-A-COOR}^2 \quad (I)$$

and are advantageously prepared from fusel oils; these are particularly suited for formulation into useful solvent, cosolvent, stripping, crystallization inhibiting, cleaning and degreasing compositions.

10 Claims, No Drawings

DICARBOXYLIC ACID DIESTERS, NOTABLY THOSE PREPARED FROM FUSEL OILS

CROSS-REFERENCE TO EARLIER APPLICATIONS

This application is a national phase of PCT/EP 2008/064179, filed Oct. 21, 2008 and designating the United States (published in the French language on Apr. 30, 2009 as WO 2009/053347 A1; the title and abstract were also published in English), which claims foreign priority under 35 U.S.C. §119 of FR 0707367, filed Oct. 22, 2007, each hereby expressly incorporated by reference in its entirety and each assigned to the assignee hereof.

A subject-matter of the present invention is novel dicarboxylic acid diesters which can in particular be obtained using fusel oil. These compounds can in particular be of use as solvents.

Compounds of dicarboxylic acid diester type have been described. Compounds deriving from fusel oil have furthermore been described. Some usages and some properties of these compounds have been described.

The document "Esterification Reaction of Oleic Acid with a Fusel Oil Fraction for Production of Lubricating Oil", Özgülsün et al., JAOCS, Vol. 77, No. 1 (2000), p. 105, describes products from the esterification of monoacids.

The document FR 2 878 157 describes the acetate of fusel oil and its use in nail varnishes as solvent having a low VOC.

The document "The Use of Egyptian Fusel Oil for the Preparation of Some Plasticizers Compatible with Polyvinyl Chloride", Chuiba et al., Indian Journal of Technology, Vol. 23, August 1985, pp. 309-311, describes a reaction product of a fusel oil having a boiling point of 110 to 136° C. and of pure adipic or sebacic acid. The plasticizing properties which were presented for these compounds are mediocre in comparison with those which were presented for the others.

Furthermore, solvents of dicarboxylic acid diester type (dibasic esters) are available commercially which are esterification products of a mixture of adipic, glutaric and succinic acid with a methyl, ethyl or isobutyl alcohol. The products sold by Rhodia are known in particular: Rhodiasolv® RPDE, which is a dimethyl ester, Rhodiasolv® DEE, which is a diethyl ester, and Rhodiasolv® DIB, which is a diisobutyl ester. These products exhibit an excellent ecological profile, excellent biodegradability and an excellent safety profile and originate from manufacturing processes which optimize the resources and which reduce the environmental impact. However, their uses are limited and there exists a need for products exhibiting a superior activity, at least with regard to certain materials. There exists in particular a need for other products exhibiting a profile which is as good or indeed even better.

The invention meets this need by providing a compound or a material composition based on dicarboxylic acid diester(s) of formula (I):

where:
- the group A represents a divalent alkylene group comprising, on average, at least 2.1 carbon atoms, preferably from 2.5 to 10 carbon atoms,
- the $R^1$ and $R^2$ groups, which are identical or different, represent a linear or branched, cyclic or noncyclic, $C_1$-$C_{20}$ alkyl, aryl, alkylaryl or arylalkyl group, characterized in that:
  at least a portion of the $R^1$ and/or $R^2$ groups are branched alkyl groups comprising 5 carbon atoms, and/or
  at least a portion of the $R^1$ and/or $R^2$ groups originate from fusel oil, with the exception of a reaction product of a fusel oil having a boiling point of 110 to 136° C. and of pure adipic or sebacic acid.

The compounds and material compositions of the invention are particularly effective in particular in removing materials of petroleum type. They make it possible to remove more of such materials and/or to remove as much material but more rapidly.

Furthermore, they exhibit an excellent ecological profile and an excellent operational safety profile and make possible excellent optimization/saving of the resources available on earth, in particular bioresources.

The invention also relates to a process for the preparation of the compounds or material compositions of the invention.

The invention also relates to the use, as solvent, cosolvent, stripper, crystallization inhibitor, cleaning agent and/or degreasing agent, of the compounds or material compositions of the invention, without the exception of the reaction product of a fusel oil having a boiling point of 110 to 136° C. and of pure adipic or sebacic acid. These compounds or material compositions are subsequently known as "useful compounds" or "useful material compositions". The useful compounds or useful material compositions can be defined as the compounds or material compositions based on dicarboxylic acid diester(s) of formula (I):

where:
- the group A represents a divalent alkylene group comprising, on average, at least 2.1 carbon atoms, preferably from 2.5 to 10 carbon atoms,
- the $R^1$ and $R^2$ groups, which are identical or different, represent a linear or branched, cyclic or noncyclic, $C_1$-$C_{20}$ alkyl, aryl, alkylaryl or arylalkyl group, characterized in that:
  at least a portion of the $R^1$ and/or $R^2$ groups are branched alkyl groups comprising 5 carbon atoms, and/or
  at least a portion of the $R^1$ and/or $R^2$ groups originate from fusel oil.

The invention also relates to a process for the preparation of the compounds or material compositions of the invention and/or of the useful compounds or useful material compositions.

The invention also relates to operating compositions comprising useful compounds or useful material compositions, in particular the compounds or material compositions of the invention. The invention also relates to processes in which a solvation, a cosolvation, a stripping, a crystallization inhibition, a cleaning and/or a degreasing is/are carried out in the presence of useful compounds or useful material compositions, in particular the compounds or material compositions of the invention. The complete process can include in particular the phase of preparing the said compounds or material compositions.

Useful compounds and useful material compositions, in particular the compounds or material compositions of the invention, are particularly effective in particular in removing materials of petroleum or asphaltene type. They make it possible to remove more of such materials and/or to remove as much material but more rapidly.

Moreover, they exhibit an excellent ecological profile and an excellent operating safety profile and make possible excellent optimization/saving of the resources available on earth, in particular bioresources.

Definitions

In the present patent application, a compound denotes a chemical substance exhibiting a single chemical formula, when it is isolated (with a purity of greater than 99% by weight).

In the present patent application, a material composition denotes a mixture of several compounds. A material composition can be defined by mentioning all or part of each of the precise chemical formulae of compounds present therein or by mentioning all or part of several general chemical formulae grouping together several compounds (families of compounds), if appropriate using means, or by mentioning a single general formula with means. A material composition comprises at least 50% by weight of compounds corresponding to the chemical formulae (precise formulae, or general formula (e), or mean formula (e)) used to define them, preferably at least 75%, preferably at least 90%, preferably at least 99%.

In the present patent application, a family of compounds denotes a group of compounds exhibiting at least one common structural characteristic, for example an identical group. A subgroup of a material composition may be concerned. It is possible, for example, to refer to a family for which the number of carbon atoms of the group A is 3, to a family where it is 4, and the like, to a family where the group A is branched, and/or to a family where the $R^1$ and/or $R^2$ groups comprise an isoamyl group, and the like.

In the present application, the number-average of a number of atoms in a material composition is given by the

where:

$x_i$ is the molar fraction of the compound under consideration or of a family under consideration, $N_i$ is the number of atoms under consideration in the compound under consideration or the family under consideration (a family under consideration groups together the same number of atoms under consideration).

If a mean number is equal to an integer, it may relate to a single compound or to a single family of compounds, exhibiting this number of atoms, or it may relate to a material composition comprising several compounds or families of compounds with different numbers of atoms, in proportions such that the mean number is equal to the integer.

Compound or Material Composition of Formula (I)

The compound or the material composition of the invention exhibits the following formula (I):

$$R^1\text{—OOC-A-COO—}R^2 \quad (I)$$

where:
 the group A represents a divalent alkylene group comprising, on average, at least 2.1 carbon atoms, preferably from 2.5 to 10 carbon atoms,
 the $R^1$ and $R^2$ groups, which are identical or different, represent a linear or branched, cyclic or noncyclic, $C_1$-$C_{20}$ alkyl, aryl, alkylaryl or arylalkyl group, characterized in that:
 at least a portion of the $R^1$ and/or $R^2$ groups are branched alkyl groups comprising 5 carbon atoms, and/or
 at least a portion of the $R^1$ and/or $R^2$ groups originate from fusel oil, with the exception of a reaction product of a fusel oil having a boiling point of 110 to 136° C. and of pure adipic or sebacic acid.

The material composition can correspond to a complex reaction product, where mixtures of reactants are used. For example, the reaction of a mixture of HOOC-$A^a$-COOH and HOOC-$A^b$-COOH with an alcohol $R^a$—OH can give a mixture of the products $R^a$OOC-$A^a$-COO$R^a$ and $R^a$OOC-$A^b$-COO$R^a$. Likewise, the reaction of HOOC-$A^a$-COOH with a mixture of alcohols $R^a$—OH and $R^b$—OH can give a mixture of the products $R^a$OOC-$A^a$-COO$R^a$ and $R^b$OOC-$A^a$-COO$R^b$, $R^a$OOC-$A^a$-COO$R^b$ and $R^b$OOC-$A^a$-COO$R^a$ (different from $R^a$OOC-$A^a$-COO$R^b$ if $A^a$ is not symmetrical). Likewise, the reaction of a mixture of HOOC-$A^a$-COOH and HOOC-$A^b$-COOH with a mixture of alcohols $R^a$—OH and $R^b$—OH can give a mixture of the products $R^a$OOC-$A^a$-COO$R^a$ and $R^b$OOC-$A^a$-COO$R^b$, $R^a$OOC-$A^a$-COO$R^b$, $R^b$OOC-$A^a$-COO$R^a$ (different from $R^a$OOC-$A^a$-COO$R^b$ if $A^a$ is not symmetrical), $R^a$OOC-$A^b$-COO$R^a$ and $R^b$OOC-$A^b$-COO$R^b$, $R^a$OOC-$A^b$-COO$R^b$ and $R^b$OOC-$A^b$-COO$R^a$ (different from $R^a$OOC-$A^b$-COO$R^b$ if $A^b$ is not symmetrical). Thus, in the case of products resulting from reactants with complex compositions, it may be appropriate to partially define the products by the reactants or their origin.

Out of practical concerns, the description of the groups can be divided up as follows:
 on the one hand, the groups $R^1$ and $R^2$, which can correspond to alcohols $R^1$—OH and $R^2$—OH (respectively). These groups can be likened to the alcohols.
 on the other hand, the group(s) A, which can correspond to one or more dicarboxylic acid(s) HOOC-A-COOH. The group(s) A can be likened to the corresponding diacid(s) (the diacid comprises 2 more carbon atoms than the group A).

Groups $R^1$ and $R^2$—Fusel Oil

The groups $R^1$ and $R^2$ can be identical or different. As set out above, the groups $R^1$ and $R^2$ can be identical if a single or pure reactant is used. If use is made of a reactant comprising several different compounds corresponding to these groups, then different compounds are obtained, the mixture of which corresponds to a material composition. It is possible in this case to distinguish families comprising at least one given group $R^1$, families comprising one and just one given group $R^1$, families comprising two given groups which are identical $R^1$=$R^2$, families comprising pairs of given groups $R^1$ and $R^2$ (these families are not necessarily mutually exclusive).

For the compounds or the material composition,
 at least a portion of the groups $R^1$ and/or $R^2$ are branched alkyl groups comprising 5 carbon atoms, and/or
 at least a portion of the groups $R^1$ and/or $R^2$ originates from fusel oil.

Fusel oil, sometimes also known as fusel alcohol, is a mixture comprising "higher order" alcohols comprising at least three carbon atoms. It is a by-product of alcoholic fermentation (in particular ethanolic fermentation) of plants. Fusel oil can in particular be produced during the distillation of ethanol after a fermentation of plants (this is carried out, for example, for the production of ethanol and/or for the production of alcoholic drinks of distilled type (degree of alcohol of greater than 50°). The operation is carried out by fermentation of the plant product, distillation of the fermentation product, for example in a distillation column, and recovery of the nonvolatile fraction, for example at the bottom of the column. The plant can in particular be beet, sugar cane, potato, sweet potato, a fruit, in particular grapes, a vegetable, a cereal, in particular wheat or barley, an oleaginous plant, rice or a mixture. The fermentation is generally intended to produce ethanol and the distillation is generally intended to recover a product with a high ethanol content. The fusel oil is the distillation residue, generally recovered as distillation column bottoms. This residue is sometimes also known as molasses. Processes for the preparation of fusel oil are known; reference is made, for example, to the document EP 624 388. The composition of the fusel oil can vary according to the processes and according to the plant fermented. The various compositions are known. Fusel oil generally comprises isoamyl alcohol (3-methylbutan-1-ol), generally in combination with other higher-order alcohols comprising at least three carbon atoms, in particular linear or branched $C_3$, $C_4$, $C_5$ (other than isoamyl alcohol) or $C_6$ alcohols, and/or with ethanol. It can in particular comprise, in addition to isoamyl alcohol, ethanol, n-butanol, isobutanol, n-amyl alcohol and n-propanol. Fusel oil can in particular comprise other compounds, such as water (in proportions generally of 1 to 20% by weight, preferably of less than 10% by weight), and impurities, such as ethers, fatty acids and furfurals (in proportions typically of less than 15% by weight, preferably of less than 10% by weight, preferably of less than 5% by weight). Fusel oils are sometimes characterized by their boiling point or by boiling point ranges. This can range from 80° C. to 150° C. Fusel oils having a boiling point within the range from 110° C. to 130° C. (or less than 130° C.) prove to be particularly useful.

It is preferable for the fusel oil to comprise at least 10% by weight, preferably at least 20% by weight, preferably at least 40% by weight, preferably at least 50% by weight and, for example, up to 70% by weight, with respect to all the alcohols present in the fusel oil, of branched alcohol(s) comprising 5 carbon atoms, preferably isoamyl alcohol. The fusel oil can typically also comprise from 5 to 40% by weight of ethanol, from 1 to 8% by weight of 1-propanol, from 0 to 1% by weight of 2-propanol, from 5 to 15% by weight of 2-methylpropanol, from 0 to 1% by weight of 1-butanol and from 10 to 30% by weight of 2-methylbutanol, with respect to all the alcohols present in the fusel oil, the proportions being such that the total is 100%.

At least a portion of the groups $R^1$ and/or $R^2$ are branched alkyls comprising 5 carbon atoms and/or originating from fusel oil. It is noted that these two characteristics are not mutually exclusive as fusel oil, as mentioned above, generally comprises at least one branched alcohol comprising 5 carbon atoms (such as isoamyl alcohol) of formula R—OH where R corresponds to such an alkyl.

The other groups $R^1$ and/or $R^2$ can in particular be linear or branched, cyclic or noncyclic, $C_1$-$C_{20}$ alkyl, aryl, alkylaryl or arylalkyl groups, other than branched alkyl groups comprising 5 carbon atoms, originating or not originating from fusel oil. They can in particular be $C_1$-$C_8$ groups, for example groups chosen from the methyl, ethyl, n-propyl, isopropyl, n-butyl, isobutyl, n-amyl, n-hexyl, cyclohexyl, 2-ethylhexyl and isooctyl groups and their mixtures.

According to a practical embodiment, use is made of a material composition comprising:
compounds of formula (I) where $R^1$ and/or $R^2$ are isoamyl groups, and
at least one compound chosen from the following compounds:
compounds where $R^1$ and/or $R^2$ are ethyl groups,
compounds where $R^1$ and/or $R^2$ are n-propyl groups,
compounds where $R^1$ and/or $R^2$ are isopropyl groups,
compounds where $R^1$ and/or $R^2$ are n-butyl groups,
compounds where $R^1$ and/or $R^2$ are isobutyl groups,
compounds where $R^1$ and/or $R^2$ are n-amyl groups,
mixtures of these compounds.

Preferably, the compound or the material composition of the invention exhibits at least 10% by weight, with respect to all groups $R^1$ and $R^2$ of the compounds corresponding to the formula (I), preferably at least 20% by weight, preferably at least 40% by weight, preferably at least 50% by weight, of groups $R^1$ and/or $R^2$ which are branched alkyl groups comprising 5 carbon atoms, preferably isoamyl groups. The amounts can be determined by analyses and/or by the amounts of reactants employed during the preparation of the compound or of the material composition. For example, if use is made of a single branched alcohol comprising 5 carbon atoms, the proportion by weight of the corresponding groups $R^1$ and $R^2$ will be 100%. If use is made of a mixture comprising a branched alcohol comprising 5 carbon atoms and another alcohol, the proportion by weight of branched alkyl groups $R^1$ and/or $R^2$ comprising 5 carbon atoms can be regarded as equal to the proportion of the corresponding alcohol in the alcohol mixture.

Use may in particular be made of a product (a material composition) capable of being obtained by reaction of a diacid of formula HOOC-A-COOH or of a diester of formula MeOOC-A-COOMe or of an acyl dichloride of formula ClOC-A-COCl or of an imide of formula

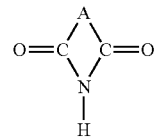

with fusel oil, for example obtained as mentioned above.
Group A

The group A is a divalent alkylene group comprising, on average, at least 2.1 carbon atoms, preferably from 2.5 to 10 carbon atoms. It can be a single group, with an integral number of carbon atoms of greater than or equal to 3, for example equal to 3 or 4, with the exception of a reaction product of a fusel oil having a boiling point of 110 to 136° C. and of pure adipic or sebacic acid. Such a single group can correspond to the use of a single acid. It can alternatively be a mixture of groups corresponding to a mixture of compounds, at least one of which exhibits at least 3 carbon atoms. Mention is made that the mixtures of groups A can correspond to mixtures of different isomeric groups comprising an identical number of carbon atoms and/or of different groups comprising different numbers of carbon atoms. The group A can comprise linear and/or branched groups.

The use of mixtures of groups A can in particular prove to be advantageous in the context of certain uses. The mixtures of groups A can in particular confer broader or more widely distributed profiles of dissolutions and/or profiles of evaporation as a function of time and/or of a temperature. Broader or more widely distributed evaporation profiles can be advantageous in the context of application of coatings in solution in solvent material compositions. Such profiles can in particular improve the quality of the coating (for example its appearance and/or its adhesion and/or its distribution over the substrate).

According to a first embodiment, at least a portion of the groups A corresponds to a group of formula —$(CH_2)_n$— where n is a mean number greater than or equal to 3 (with the exception of a reaction product of a fusel oil having a boiling point of 110 to 136° C. and of pure adipic or sebacic acid). At least a portion of the groups A can be groups of formula —$(CH_2)_3$— (the corresponding acid is glutaric acid). In a specific alternative form of this first embodiment, the groups A comprise a mixture of a group of formula —$(CH_2)_4$— (the corresponding acid is adipic acid) and of a group of formula —$(CH_2)_3$—.

Thus, use may be made of a material composition comprising:
compounds of formula (I) where A is a group of formula —$(CH_2)_4$—, and/or
compounds of formula (I) where A is a group of formula —$(CH_2)_3$—.

Use may in particular be made of a material composition comprising:
compounds of formula (I) where A is a group of formula —$(CH_2)_4$—,
compounds of formula (I) where A is a group of formula —$(CH_2)_3$—, and
compounds of formula (I) where A is a group of formula —$(CH_2)_2$—.

Use may preferably be made of a material composition comprising (the total number of moles of the three types of compounds being 100%):
from 1 to 20%, preferably from 5 to 15%, in moles, of compounds of formula (I) where A is a group of formula —$(CH_2)_4$—,
from 45 to 75%, preferably from 55 to 65%, in moles, of compounds of formula (I) where A is a group of formula —$(CH_2)_3$—, and
from 15 to 45%, preferably from 20 to 33%, in moles, of compounds of formula (I) where A is a group of formula —$(CH_2)_2$—.

According to a second embodiment, at least a portion of the groups A corresponds to a branched group. In particular, the group A can be chosen from:
the group $A_{MG}$ of formula —$CH(CH_3)$—$CH_2$—$OH_2$—,
the group $A_{ES}$ of formula —$CH(C_2H_5)$—$CH_2$—, and
mixtures thereof.

It is not ruled out for a portion of the groups to correspond to linear groups of formula —$(CH_2)_n$— where n is a mean number greater than or equal to 3, for example equal to 4.

Use may in particular be made of a material composition comprising (the total number of moles of the three types of compounds being 100%):
from 70 to 95%, preferably from 75 to 90%, in moles, of compounds of formula (I) where A is a group $A_{MG}$,
from 5 to 30%, preferably from 5 to 20%, in moles, of compounds of formula (I) where A is a group $A_{ES}$, and
from 0 to 10%, in moles, of compounds of formula (I) where A is a group of formula —$(CH_2)_4$—.

Specific Compounds or Material Compositions

Specific compounds of the invention, optionally included in material compositions, are as follows:
$R_{IA}$—$(CH_2)_3$—$R_{IA}$
$R_{IA}$—$(CH_2)_3$—$R_{Et}$
$R_{IA}$—$(CH_2)_3$—$R_{Pr}$
$R_{IA}$—$(CH_2)_3$—$R_{MB}$
$R_{IA}$—$CH(CH_3)$—$CH_2$—$CH_2$—$R_{IA}$
$R_{IA}$—$CH(CH_3)$—$CH_2$—$CH_2$—$R_{Et}$
$R_{IA}$—$CH(CH_3)$—$CH_2$—$CH_2$—$R_{Pr}$
$R_{IA}$—$CH(CH_3)$—$CH_2$—$CH_2$—$R_{MB}$
$R_{Et}$—$CH(CH_3)$—$CH_2$—$CH_2$—$R_{IA}$
$R_{Pr}$—$CH(CH_3)$—$CH_2$—$CH_2$—$R_{IA}$
$R_{MB}$—$CH(CH_3)$—$CH_2$—$CH_2$—$R_{IA}$
$R_{IA}$—$CH(C_2H_5)$—$CH_2$—$R_{IA}$
$R_{IA}$—$CH(C_2H_5)$—$CH_2$—$R_{Et}$
$R_{IA}$—$CH(C_2H_5)$—$CH_2$—$R_{Pr}$
$R_{IA}$—$CH(C_2H_5)$—$CH_2$—$R_{MB}$
$R_{Et}$—$CH(C_2H_5)$—$CH_2$—$R_{IA}$
$R_{Pr}$—$CH(C_2H_5)$—$CH_2$—$R_{IA}$
$R_{MB}$—$CH(C_2H_5)$—$CH_2$—$R_{IA}$ where
$R_{IA}$ is an isoamyl group
$R_{Et}$ is an ethyl group
$R_{Pr}$ is an n-propyl or isopropyl group
$R_{MB}$ is a 2-methylbutyl group.

Use may in particular be made of a material composition comprising:
compounds of formula (I) where A is a group of formula —$(CH_2)_4$— and where $R^1$ and/or $R^2$ are isoamyl groups; and
compounds of formula (I) where A is a group of formula —$(CH_2)_3$— and where $R^1$ and/or $R^2$ are isoamyl groups.

Use may in particular be made of a material composition comprising:
compounds of formula (I) where the group A is a group of formula $A_{MG}$ and where $R^1$ and/or $R^2$ are isoamyl groups, and
compounds of formula (I) where the group A is a group of formula $A_{ES}$ and where $R^1$ and/or $R^2$ are isoamyl groups.

Specific material compositions of the invention are as follows:
Composition comprising the following compounds:
$R_{IA}$—$(CH_2)_3$—$R_{IA}$
$R_{IA}$—$(CH_2)_4$—$R_{IA}$
$R_{IA}$—$(CH_2)_2$—$R_{IA}$
and optionally:
$R_{IA}$—$(CH_2)_3$—$R_{Et}$
$R_{IA}$—$(CH_2)_3$—$R_{Pr}$
$R_{IA}$—$(CH_2)_3$—$R_{MB}$
$R_{IA}$—$(CH_2)_4$—$R_{Et}$
$R_{IA}$—$(CH_2)_4$—$R_{Pr}$
$R_{IA}$—$(CH_2)_4$—$R_{MB}$
$R_{IA}$—$(CH_2)_2$—$R_{Et}$
$R_{IA}$—$(CH_2)_2$—$R_{Pr}$, and/or
$R_{IA}$—$(CH_2)_2$—$R_{MB}$ Composition comprising the following compounds:
$R_{IA}$—$CH(CH_3)$—$CH_2$—$CH_2$—$R_{IA}$
$R_{IA}$—$CH(C_2H_5)$—$CH_2$—$R_{IA}$
and optionally:
$R_{IA}$—$(CH_2)_4$—$R_{IA}$
$R_{IA}$—$CH(CH_3)$—$CH_2$—$CH_2$—$R_{Et}$
$R_A$—$CH(CH_3)$—$CH_2$—$CH_2$—$R_{Pr}$
$R_{IA}$—$CH(CH_3)$—$CH_2$—$CH_2$—$R_{MB}$
$R_{Et}$—$CH(CH_3)$—$CH_2$—$CH_2$—$R_{IA}$
$R_{Pr}$—$CH(CH_3)$—$CH_2$—$CH_2$—$R_{IA}$
$R_{MB}$—$CH(CH_3)$—$CH_2$—$CH_2$—$R_{IA}$
$R_{IA}$—$CH(C_2H_5)$—$CH_2$—$R_{Et}$
$R_{Et}$—$CH(C_2H_5)$—$CH_2$—$R_{Pr}$
$R_{IA}$—$CH(C_2H_5)$—$CH_2$—$R_{MB}$
$R_{Et}$—$CH(C_2H_5)$—$CH_2$—$R_{IA}$
$R_{Pr}$—$CH(C_2H_5)$—$CH_2$—$R_{IA}$
$R_{MB}$—$CH(C_2H_5)$—$CH_2$—$R_{IA}$
$R_{IA}$—$(CH_2)_4$—$R_{Et}$
$R_{IA}$—$(CH_2)_4$—$R_{Pr}$ and/or
$R_{IA}$—$(CH_2)_4$—$R_{MB}$.

Processes

The useful compounds or useful material compositions can be prepared by any appropriate process. A process for preparing the adduct of adipic acid and of fusel oil is, for example, described in the document "The Use of Egyptian Fusel Oil for the Preparation of Some Plasticizers Compatible with Polyvinyl Chloride", Chuiba et al., Indian Journal of Technology, Vol. 23, August 1985, pp. 309-311. Use may be made of a similar process, if appropriate (for the compounds or material compositions of the invention), by replacing the adipic acid with another diacid or with a mixture of diacids of formula HOOC-A-COOH.

The compounds or material compositions can, for example, be obtained by a process comprising an "esterification" stage by reaction of a diacid of formula HOOC-A-COOH or of a diester of formula MeOOC-A-COOMe or of an acyl dichloride of formula ClOC-A-COCl or of an imide of formula

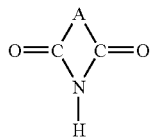

with:
a branched alcohol comprising 5 carbon atoms or a mixture of alcohols comprising a branched alcohol comprising 5 carbon atoms, preferably isoamyl alcohol or a material composition comprising isoamyl alcohol, and/or
fusel oil.

It is possible in particular to employ a mixture of diacids, diesters, acyl dichlorides or imides.

The reactions can be appropriately catalysed. Use is preferably made of at least 2 molar equivalents of alcohols per diacid, diester, acyl dichloride or imide. It is possible, for example, to employ from 2 to 2.5 equivalents for the reactions with the diacids, diesters or acyl dichlorides. It is possible, for example, to employ from 5 to 25, for example from 10 to 20, equivalents for the reactions with the imides. The reactions can, if appropriate, be promoted by extraction of the reaction by-products (for example, extraction by evaporation of the methanol during a transesterification starting from the diester).

The reaction can be followed by stages of filtration and/or of purification, for example by distillation.

The alcohol or the mixture of alcohols can be represented by the formula R—OH, where R represents a group $R^1$ or $R^2$ or a mixture of groups $R^1$ and $R^2$. Such groups and corresponding alcohols have been described above. Fusel oil has also formed the subject of a description above.

According to a useful form, the operation is carried out by reaction with a diacid or a mixture of diacids. It is also possible to operate by reaction with a "light" diester of formula Me-OOC-A-COOMe. In this case, the operation is more specifically a transesterification, starting from a light diester, in order to obtain a heavier diester in accordance with the invention. Diacids or mixtures of diacids have been described above (by the group A) and are commercially available. Use may in particular be made of a mixture of adipic acid, glutaric acid and succinic acid, normally referred to as "AGS". A mixture of light diesters, such as a mixture of dimethyl adipate, dimethyl glutarate and dimethyl succinate, for example sold by Rhodia under the name Rhodiasolve® RPDE can be employed for the transesterification reaction.

According to a specific form, use is made, as reactant, of 2-methylglutaric acid, or of a mixture of 2-ethylsuccinic acid and 2-methylglutaric acid, or of a mixture of 2-ethylsuccinic acid, 2-methylglutaric acid and adipic acid, or of the corresponding diesters. The diacids in the form of mixtures can in particular be obtained from a mixture of dinitrile compounds in particular produced and recovered in the process for the manufacture of adiponitrile by double hydrocyanation of butadiene. This process, used on a large scale industrially to produce the greater majority of the adiponitrile consumed worldwide, is described in numerous patents and works. The reaction for the hydrocyanation of butadiene results predominantly in the formulation of linear dinitriles but also in formation of branched dinitriles, the two main ones of which are methylglutaronitrile and ethylsuccinonitrile. The branched dinitrile compounds are separated by distillation and recovered, for example, as top fraction in a distillation column, in the stages for separation and purification of the adiponitrile. The branched dinitriles can subsequently be converted to diacids or diesters (either to light diesters, for a subsequent transesterification reaction with the alcohol or the mixture of alcohols or the fusel oil, or directly to diesters in accordance with the invention).

One of the possible processes for the conversion of the dinitriles to diesters corresponds to the use of the Pinner reaction, described in particular in French Patent No. 1 488 857. Basically, this process consists in reacting the dinitrile compounds with an alcohol in the presence of a strong inorganic acid, such as sulphuric acid, and in then hydrolysing the products obtained in order to recover diesters by distillation. This document also describes a specific embodiment of the process which consists in passing the mixture of dinitrile compounds and the alcohol into a bath of molten salts based on various alkali metal and ammonium sulphates, in order to avoid the formation of ammonium sulphate and to recover the ammonia by extraction with steam. Useful diesters can also be obtained by reaction between the dinitrile compounds, water and an alcohol in the gas phase and in the presence of a solid catalyst. The reaction temperature is advantageously greater than the condensation temperature of the diesters formed. Use may be made, as catalyst, of a solid acid catalyst, such as, for example, a silica gel, a silica/alumina mixture or supported boric or phosphoric acids. Use may also be made of macroporous aluminas, such as those described in the document EP 805 801. The reaction temperature for the conversion of dinitriles to diesters can be between 200° C. and 450° C., preferably between 230° C. and 350° C. The reaction can be carried out under any pressure, advantageously of between 0.1 and 20 bar. At the outlet of the reactor, the vapours can be rapidly cooled to a temperature of less than or equal to 150° C. The ammonia, then the water and the excess alcohol can be separated by distillation from the mixture obtained. Useful diesters can also be obtained by reaction between the dinitrile compounds and an inorganic base, in order to obtain acid salts, then neutralization of these salts with an acid, followed by an esterification with an alcohol. A useful process is described in detail in particular in the French patent application filed on 9 Jun. 2006 under No. 0605119.

Useful diacids can be obtained by reaction between the dinitrile compounds and an inorganic base, in order to obtain acid salts, followed by neutralization of these salts by an acid. Useful diacids can also be obtained by acid hydrolysis of the dinitrile compounds. Details with regard to such reactions are given in the following documents:
patent application published under No. WO2007/101929,
French patent application filed on 9 Jun. 2006 under No. 0605119,
French patent application filed on 24 Nov. 2006 under No. 0610302.

According to a specific form, use is made of a reactant which is an imide or mixture of imides. The esterification reaction can be carried out in the gas phase at a high temperature, for example from 250 to 300° C., if appropriate in the presence of a catalyst, such as $TiO_2$, $ZrO_2$ or $CeO_2$. The imide or the mixture of imides can in particular be obtained from a dinitrile or a mixture of dinitriles by an "imidation" reaction by reaction of a dinitrile or a mixture of dinitriles of formula NC-A-CN with water in the gas phase, if appropriate in the presence of a catalyst, such as $TiO_2$. The esterification reaction can be subsequent to or simultaneous with the imidation reaction. Use may in particular be made, as imides, of 2-methylglutarimide, ethylsuccinimide, mixtures of 2-methylglutarimide and ethylsuccinimide, and mixtures of 2-methylglutarimide, ethylsuccinimide and adipimide. Details with regard to the reactions where imides or mixtures of imides are employed are given in the PCT patent application filed on 5 Jul. 2007 under No. PCT/FR2007/001140, included as reference.

Uses

The useful compounds or useful material compositions can in particular be used as solvents, cosolvents, strippers, crystallization inhibitors, cleaning agents and/or degreasing agents.

The term "cosolvent" is understood to mean that other solvents can be combined with it. The use as solvent or cosolvent comprises in particular uses for dissolving a compound in a formulation or in a reaction medium, the use for completely or partially dissolving a product to be removed (degreasing, stripping) and/or the use for facilitating the detachment of films of materials.

The useful compounds or useful material compositions can in particular be used, for the functions indicated above or for others, in a plant protection formulation, in a cleaning formulation, in a stripping formulation, in a degreasing formulation, in a lubricating formulation, in a coating formulation, in a pigment or ink formulation or in a plastic formulation. The cleaning and/or degreasing formulations can in particular be formulations for household care, worked in homes or in public areas (hotels, offices, factories, and the like). They can be formulations for cleaning hard surfaces, such as floors, surfaces of furniture and of kitchen and bathroom fittings, or dishes. These formulations can also be used in the industrial sphere for degreasing manufactured products and/or cleaning them.

The useful compounds or useful material compositions can in particular be used to remove, from a substrate, a contaminant, a coating or an agent for helping in the manufacture. It can, for example, be a matter of removing paint, of removing a residue of a plastic mould used in casting, of removing graffiti or of removing residues of lubricants or films used to manufacture or protect manufactured items, in particular made of metal. It can be a matter of removing a product, for example a coating, from tools used to apply a product. The product remaining on the tool can furthermore be regarded as a contaminant. It can be in particular asphalt to be removed from applicational tools or from storage and/or transportation means. The contaminant can in particular be crude petroleum or asphaltenes. For these contaminants, the substrate can, for example, be a polluted shore which it is desired to clean, a textile or a surface on a site for the extraction of oil and/or gas (an oil platform, for example), which it is desired to clean for reasons of health and/or safety.

The useful compounds or useful material compositions can in particular be used in plant protection formulations comprising a solid active product.

Other details or advantages may become apparent in the light of the examples which follow, without a limiting nature.

EXAMPLES

Use is made in particular of the following starting materials:

Fusel oil 1: Fusel oil available from Wako with a boiling point of 110-130° C. and with a density of 0.810-0.850.

Isoamyl alcohol: Prolabo

AGS: Mixture comprising adipic acid (12.5 mol %), glutaric acid (62.5 mol %) and succinic acid (24.5 mol %)

MGA: Mixture comprising 2-methylglutaric acid (86 mol %), ethylsuccinic acid (11 mol %) and adipic acid (3 mol %)

MGI: Mixture comprising 2-methylglutarimide (88.5 mol %) and ethylsuccinimide (11.5 mol %)

Example 1

Preparation of Material Compositions Resulting from the Esterification of a Fusel Oil and of AGS. "AGS isoamyl"

Example 1.1

Esterification in the Presence of Sulphuric Acid

Fusel oil 1 (280 g) and then the AGS (200 g) and 2 g of sulphuric acid are successively introduced into a 1 l reactor. The reaction mixture is heated while being stirred. During the heating, water is distilled off while entraining a small amount of residual light alcohols. The reaction medium is maintained at 120° C. for 3 hours. After heating for 3 hours, the temperature of the medium is brought back to ambient temperature. The medium is then washed with an aqueous sodium hydrogencarbonate solution. The organic phase comprises 92% of diesters. It is subsequently distilled at 180-190° C. under a pressure of 20 mmHg in order to obtain a product comprising 99-100% by weight of diesters.

Example 1.2

Esterification in the Presence of Clay

The esterification is carried out according to Example 1.1 but using 5 g of K10 clay from aid Chemie instead of the sulphuric acid. The reaction is carried out at 130° C. for 3 h 30. The reaction medium is subsequently filtered at 80° C. under 1 bar in order to remove the clay. The organic phase then comprises 85% of diesters. It is subsequently distilled at 180-190° C. under a pressure of 20 mmHg in order to obtain a product comprising 99-100% by weight of diesters.

Example 1.3

Esterification in the Presence of Amberlyst 15 Resin

The esterification is carried out according to Example 1.1 but using 5 g of Amberlyst 15 resin instead of the sulphuric acid. The reaction is carried out at 130° C. for 3 h 30. The reaction medium is subsequently filtered at 80° C. under 1 bar in order to remove the resin. The organic phase then comprises 85% of diesters. It is subsequently distilled at 180-190° C. under a pressure of 20 mmHg in order to obtain a product comprising 99-100% by weight of diesters.

Example 1.4

Esterification in the Presence of HY 720 Zeolite

The esterification is carried out according to Example 1.1 but using 5 g of HY 720 zeolite instead of the sulphuric acid. The reaction is carried out at 130° C. for 3 h 30. The reaction medium is then filtered at 80° C. under 1 bar in order to remove the zeolite. The organic phase then comprises 89% of diesters. It is subsequently distilled at 180-190° C. under a pressure of 20 mmHg in order to obtain a product comprising 99-100% by weight of diesters.

Example 2

Preparation of a Material Composition Resulting from a Fusel Oil and MGA

As above, the amount of fusel oil is adjusted according to its quality and the acid number of the MGA used. In all cases, an excess of fusel oil is used (2.2 to 2.4 mol of fusel oil per 1 mol of MGA), so as to obtain virtually complete conversion of the MGA.

Example 2.1

Esterification in the Presence of Sulphuric Acid

Fusel oil 1 (280 g) and then the MGA (210 g) and 2 g of sulphuric acid are successively introduced into a 1 l reactor. The reaction mixture is heated while being stirred. During the heating, water is distilled off while entraining a small amount of residual light alcohols. The reaction medium is maintained at 120° C. for 3 hours. After heating for 3 hours, the temperature of the medium is brought back to ambient temperature. The medium is then washed with an aqueous sodium hydrogencarbonate solution. The organic phase comprises 93% of diesters. It is subsequently distilled at 180-190° C. under a pressure of 20 mmHg in order to obtain a product comprising 99-100% by weight of diesters.

Example 2.2

Esterification in the Presence of HY 720 Zeolite

The esterification is carried out according to Example 2.1 but using 5 g of HY 720 zeolite instead of the sulphuric acid. The reaction is carried out at 130° C. for 3 h 30. The reaction medium is subsequently filtered at 80° C. under 1 bar in order to remove the zeolite. The organic phase then comprises 88% of diesters. It is subsequently distilled at 180-190° C. under a pressure of 20 mmHg in order to obtain a product comprising 99-100% by weight of diesters.

Example 2.3

Esterification in the Presence of K10 Clay

The esterification is carried out according to Example 2.1 but using 5 g of K10 clay from Süd Chemie instead of the sulphuric acid. The reaction is carried out at 130° C. for 3 h 30. The reaction medium is subsequently filtered at 80° C. under 1 bar in order to remove the clay. The organic phase then comprises 87% of diesters. It is subsequently distilled at 180-190° C. under a pressure of 20 mmHg in order to obtain a product comprising 99-100% by weight of diesters.

Example 2.4

Esterification in the Presence of Amberlyst 15 Resin

The esterification is carried out according to Example 2.1 but using 5 g of Amberlyst 15 resin instead of the sulphuric acid. The reaction is carried out at 130° C. for 3 h 30. The reaction medium is subsequently filtered at 80° C. under 1 bar in order to remove the resin. The organic phase then comprises 85% of diesters. It is subsequently distilled at 180-190° C. under a pressure of 20 mmHg in order to obtain a product comprising 99-100% by weight of diesters.

Example 3

Preparation of a Material Composition Resulting from a Fusel Oil and MGI

Example 3.1

Reaction in the Liquid Phase—Anatase $TiO_2$ Acid Catalyst 25 g of MGI are introduced into a 300 ml pressure-resistant stainless steel reactor and 50 g of fusel oil 1 and 1 g of anatase titanium oxide (source: Millenium) are added. The reactor is closed and the reaction medium is heated to 250° C. with stirring. The reactor is purged every hour to remove the gaseous ammonia formed. After reacting for 5 hours, the conversion of the imides is complete. The reaction medium is filtered in order to recover the catalyst and the filtrate is distilled in order to separate the excess fusel oil and the mixture of diesters. The mixture of diesters is subsequently distilled at 180-190° C. under a pressure of 20 mmHg.

Example 3.2

Reaction in the Liquid Phase—Anatase $TiO_2$ Acid Catalyst

The esterification is carried out as in Example 3.1 but using a reactor equipped with a device for continuously purging ammonia. After reacting for 4 h, a mixture of diesters is obtained.

Example 3.3

Reaction in the Gas Phase—Anatase $TiO_2$ Acid Catalyst 20 ml of anatase titanium oxide in the extruded form (source: Engelhart) are introduced into a tubular reactor with a diameter of 30 mm. 10 ml of glass powder are added onto the top of the catalyst as vaporizer-static mixer. This catalytic bed is heated to 250° C. under a stream of nitrogen of 3 l/h. After conditioning for 2 hours under these conditions, a 20% w/w solution of MGI in fusel oil 1 is introduced at a flow rate of 3 ml/hour. The gases are subsequently condensed in a receiver immersed in an ice bath. After reacting for 20 hours, a mixture of diesters is obtained.

Example 3.4

Reaction in the Liquid Phase—Anatase $TiO_2$ Acid Catalyst 25 g of MGI are introduced into a 300 ml pressure-resistant stainless steel reactor and 200 g of Prolabo isoamyl alcohol assaying a purity of 99% and 1 g of anatase titanium oxide (source: Millenium) are added. The reactor is closed and the reaction medium is heated to 250° C. with stirring. The reactor is purged every hour in order to remove the gaseous ammonia formed. After reacting for 5 hours, the conversion of the MGI is virtually complete. The reaction medium is filtered in order to recover the catalyst and the filtrate is distilled in order to separate the excess fusel oil and the mixture of diesters. The mixture of diesters is distilled in the range 160-200° C. under a pressure of 20 mmHg.

Example 4

Use for Dissolving Petroleum

Products Used:
　Heavy crude petroleum—origin Brazil
　Solvents:
　　"DIB": Rhodiasolv® DIB, sold by Rhodia
　　"AGS fusel": Product resulting from Example 1.1.
Procedure
1—Preparation of a mother solution comprising 0.67% of crude petroleum from Brazil in toluene: 0.530 g of crude petroleum is dissolved in 79 g of toluene at ambient temperature.
2—Preparation of the test flasks for monitoring the kinetics: 4 g of the mother solution prepared in 1 are incorporated in 40 ml glass flasks. These flasks are placed in an oven at 80° C. overnight. After evaporating the toluene, the equivalent of 27 mg of crude petroleum remains at the bottom of the flasks in the form of a thin film.
3—Monitoring of the rate of dissolution by measurement of optical transmission Optical transmission is measured at a wavelength of 600 nm using a Metrohm phototrode connected to a photometer.
A magnetic bar is placed on the bottom of the flask comprising the thin film of crude petroleum (preparation 4-2). The assembly is placed on a magnetic stirrer at ambient temperature.
The time "zero" for the acquisition of the optical transmission signal is triggered when 30 ml of the solvent to be studied are poured into the flask comprising the 27 mg of heavy petroleum.
Results
The lower the transmission, the greater the proportion of dissolved heavy petroleum. The transmission (in %) as a function of time is given in Table 1.
The product of the invention makes greater and faster dissolution possible.

TABLE 1

|  | 0 | 1 min | 1.5 min | 2 min | 3 min | 4 min | 5 min |
|---|---|---|---|---|---|---|---|
| DIB (comparative) | 100 | 15.5 | 11.7 | 10 | 9.8 | 9.6 | 9.5 |
| AGS fusel | 100 | 12 | 9.5 | 8 | 6.5 | 6 | 6 |

It is apparent that the product in accordance with the invention makes faster dissolution possible.

Example 5

Use for Dissolving Asphaltenes

Products Used:
　Asphaltene (crude petroleum fraction rich in aromatics)
　Solvents:
　　"DIB": Rhodiasolv® DIB, sold by Rhodia
　　"IPG": mixture of glycerol and acetone
　　"MIPG": mixture of glycerol and MIBK (methyl isobutyl ketone)
　　"AGS fusel": product resulting from Example 1.1.
27 mg of asphaltenes and 30 ml of solvent are mixed. The transmission after 12 hours at 50° C., obtained with different solvents, is given below:
　DIB (comparative): 28%
　AGS fusel: 1%
　IPG (comparative): 70%
　MIPG (comparative): 60%
　Toluene (comparative): 0.2%
It is apparent that the product in accordance with the invention makes excellent dissolution possible, of the same order as that obtained with toluene, the ecotoxicological profile of which is not so good.

Example 6

Use for Cleaning/Degreasing Metal Surfaces

Products Used:
　Product to be cleaned:
　　Liquid paraffin: Catanex T121 sold by Shell
　　Heavy crude petroleum—origin Brazil
　　Solvent: "AGS fusel": Product resulting from Example 1.1.
Procedure
Liquid paraffin is deposited at ambient temperature on a steel plate, so as to cover the whole of the plate. The plate is left standing at ambient temperature for 24 h.
Petroleum is likewise deposited on another steel plate, but at 50° C. The plate is left standing in an oven at 50° C. for 24 h.
Each of the plates is dipped in the solvent, at ambient temperature for the plate with liquid paraffin and at 50° C. for the plate with petroleum.
Every 30 seconds, the plates are removed from the cleaning solution, they are passed under a thin stream of cold water (2 liters/minute) and the relative surface area of water film, with respect to the entire surface area of the plate, remaining on the plates after 1 minute in the open air is observed visually. This relative surface area is regarded as being the percentage of liquid paraffin or petroleum extracted.
Results
It is observed, on the plate carrying the liquid paraffin, that 80% of the liquid paraffin has been extracted after 4 minutes. On the plate carrying the petroleum, 100% of the petroleum has been extracted after 1 minute.

The invention claimed is:
1. A composition which comprises en admixture of dicarboxylic acid diester compounds having the structural formula (I):

$$R^1\text{—OOC-A-COO—}R^2 \qquad (I)$$

wherein:
　the $R^1$ and $R^2$ radicals, which may be identical or different, are each a linear or branched, cyclic or acyclic; $C_1$-$C_{20}$ alkyl, aryl, alkylaryl or arylalkyl radical,
　with the proviso that at least one of the $R^1$ and/or $R^2$ radicals is a branched alkyl radical having 5 carbon atoms and/or at least a fraction of the $R^1$ and/or $R^2$ radicals is derived from fusel oil, other than a reaction product of a fusel oil having a boiling point ranging from 100° to 136° C. and of a pure adipic or sebacic acid;
wherein said composition comprises:
　from 1 to 20% in moles of compounds of formula (I) where A is a group of formula —$(CH_2)_4$—,
　from 45 to 75% in moles of compounds of formula (I) where A is a group of formula —$(CH_2)_3$—, and
　from 15 to 45% in moles of compounds of formula (I) where A is a group of formula —$(CH_2)_2$—,
and wherein the composition comprises the compounds having the formulae $R_{IA}OOC$—$(CH_2)_3$—$COOR_{IA}$ and $R_{IA}OOC$—$(CH_2)_4$—$COOR_{IA}$, $R_{IA}$, being isoamyl group.
2. The composition as defined by claim 1, wherein the compounds are obtained by reacting a diacid of formula HOOC-A-COOH or of a diaster of formula MeOOC-A-COOMe or of an acyl dichloride of formula ClOC-A-COCl or of an imide of formula:

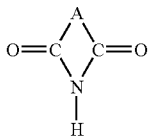

with fusel oil.

3. The composition as defined by claim 2, wherein the fusel oil is prepared by fermentation of a plant, distillation of the fermentation product, in a distillation column, and recovery of the nonvolatile fraction at the bottom of the column.

4. The composition as defined by claim 3, wherein the plant is beet, sugar cane, potato, sweet potato, a fruit, a vegetable, a cereal, an oleaginous plant, rice or a mixture thereof.

5. A process for the preparation of a compound or of a composition as defined by claim 1, comprising an esterification stage by reaction of a diacid or a mixture of diacids of formula HOOC-A-COOH or of a diester or a mixture of diesters of formula MeOOC-A-COOMe or of an acyl dichloride or a mixture of acyl dichlorides of formula ClOC-A-COCl or of an imide or a mixture of imides of formula

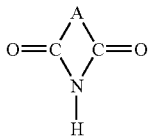

with:
a branched alcohol having 5 carbon atoms or a mixture of alcohols comprising a branched alcohol having 5 carbon atoms, and/or
fusel oil.

6. The process as defined by claim 5, wherein the imide or the mixture of imides is prepared by an imidation reaction by reaction of a dinitrile or a mixture of dinitriles NC-A-CN with water, the esterification reaction being subsequent to or simultaneous with the imidation reaction.

7. A solvent, cosolvent, stripper, crystallization inhibitor, lubricating, pigment, ink, plastic, coating, plant protection, cleaning and/or degreasing formulation comprising a composition as defined by claim 1.

8. A process for removing, from a substrate, a contaminant, a coating or a residue, comprising treating same with a formulation as defined by claim 7.

9. The process as defined by claim 8, comprising removing a contaminant which comprises a crude petroleum or an asphaltene.

10. The composition as defined by claim 1, which further comprises at least one of the following compounds:

$R_{IA}OOC-(CH_2)_2-R_{IA}$,
$R_{IA}OOC-(CH_2)_3-COOR_{Et}$,
$R_{IA}OOC-(CH_2)_3-COOR_{Pr}$,
$R_{IA}OOC-(CH_2)_3-COOR_{MB}$,
$R_{IA}OOC-(CH_2)_4-COOR_{Et}$,
$R_{IA}OOC-(CH_2)_4-COOR_{Pr}$,
$R_{IA}OOC-(CH_2)_4-COOR_{MB}$,
$R_{IA}OOC-(CH_2)_2-COOR_{Et}$,
$R_{IA}OOC-(CH_2)_2-COOR_{Pr}$, and
$R_{IA}OOC-(CH_2)_2-COOR_{MB}$;

wherein
$R_{IA}$ is an isoamyl group,
$R_{MB}$ is a 2-methyl-butyl group,
$R_{Pr}$ is a n-propyl or isopropyl group, and
$R_{Et}$ is an ethyl group.

* * * * *